US012188047B2

(12) United States Patent  
Reubinoff et al.

(10) Patent No.: US 12,188,047 B2  
(45) Date of Patent: Jan. 7, 2025

(54) PREPARATION OF RETINAL PIGMENT EPITHELIUM CELLS

(71) Applicants: CELL CURE NEUROSCIENCES LTD., Jerusalem (IL); HADASIT MEDICAL RESEARCH SERVICES AND DEVELOPMENT LTD., Jerusalem (IL)

(72) Inventors: Benjamin Eithan Reubinoff, Doar-Na HaEla (IL); Orna Singer, Jerusalem (IL); Osnat Bohana-Kashtan, Tel-Mond (IL); Ofer Wiser, Jerusalem (IL)

(73) Assignees: HADASIT MEDICAL RESEARCH SERVICES AND DEVELOPMENT LTD., Jerusalem (IL); CELL CURE NEUROSCIENCES LTD., Jerusalem (IL)

( * ) Notice: Subject to any disclaimer, the term of this patent is extended or adjusted under 35 U.S.C. 154(b) by 0 days.

(21) Appl. No.: 15/771,046

(22) PCT Filed: Oct. 26, 2016

(86) PCT No.: PCT/IL2016/051155  
§ 371 (c)(1),  
(2) Date: Apr. 25, 2018

(87) PCT Pub. No.: WO2017/072763  
PCT Pub. Date: May 4, 2017

(65) Prior Publication Data  
US 2018/0312805 A1 Nov. 1, 2018

Related U.S. Application Data

(60) Provisional application No. 62/246,214, filed on Oct. 26, 2015.

(51) Int. Cl.  
*C12N 5/079* (2010.01)  
*C12N 5/00* (2006.01)  
*C12N 5/0735* (2010.01)  
*G01N 33/53* (2006.01)

(52) U.S. Cl.  
CPC ......... *C12N 5/0621* (2013.01); *C12N 5/0018* (2013.01); *C12N 5/0606* (2013.01); *C12N 2501/15* (2013.01); *C12N 2501/16* (2013.01); *C12N 2501/999* (2013.01); *C12N 2506/02* (2013.01); *C12N 2506/45* (2013.01); *C12N 2509/00* (2013.01); *C12N 2533/52* (2013.01); *C12N 2533/54* (2013.01); *G01N 33/53* (2013.01)

(58) Field of Classification Search  
CPC .. C12N 5/0621; C12N 5/0606; C12N 5/0018; C12N 2501/15; C12N 2509/00; C12N 2533/54; C12N 2533/52; C12N 2501/16; G01N 33/53  
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | Mcconnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands et al. |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,755,785 A | 5/1998 | Rowsey et al. |
| 5,843,780 A | 12/1998 | Thomson |
| 5,941,250 A | 8/1999 | Aramant et al. |
| 5,962,027 A | 10/1999 | Hughes |
| 6,045,791 A | 4/2000 | Liu |
| 6,090,622 A | 7/2000 | Gearhart et al. |

(Continued)

FOREIGN PATENT DOCUMENTS

| | | |
|---|---|---|
| CN | 101688178 A | 3/2010 |
| CN | 102618488 A | 8/2012 |

(Continued)

OTHER PUBLICATIONS

Idelson et al. Directed Differentiation of Human Embryonic Stem Cells into Functional Retinal Pigment Epithelium Cells. Cell Stem Cell (2009), 5, 396-408. (Year: 2009).*  
Ben Dor et al. Lentiviral Vectors Harboring a Dual-Gene System Allow High and Homogeneous Transgene Expression in Selected Polyclonal Human Embryonic Stem Cells. Molecular Therapy (2006), 14(2), 255-267.. (Year: 2006).*  
Brandl et al. In-Depth Characterisation of Retinal Pigment Epithelium (RPE) Cells Derived from Human Induced Pluripotent Stem Cells (hiPSC). Neuromol Med (epub. May 2014), 16, 551-564. (Year: 2014).*  
Hughes et al. Matrigel: A complex protein mixture required for optimal growth of cell culture. Proteomics (2010), 10, 1886-1890. ( Year: 2010).*  
Natunen et al. The binding specificity of the marker antibodies Tra-1-60 and Tra-1-81 reveals a novel pluripotency-associated type 1 lactosamine epitope. Glycobiology (2011), 21(9), 1125-1130. (Year: 2011).*

(Continued)

*Primary Examiner* — Sean C. Barron  
(74) *Attorney, Agent, or Firm* — MINTZ, LEVIN, COHN, FERRIS, GLOVSKY AND POPEO, P.C.

(57) ABSTRACT

A method of generating retinal pigment epithelium cells is disclosed. Cell populations comprising same and uses thereof are also disclosed.

29 Claims, 9 Drawing Sheets

(56) References Cited

U.S. PATENT DOCUMENTS

| | | | |
|---|---|---|---|
| 6,117,675 A * | 9/2000 | van der Kooy | A61K 35/44 |
| | | | 435/384 |
| 7,112,437 B2 | 9/2006 | Pera | |
| 8,956,866 B2 | 2/2015 | Idelson et al. | |
| 11,090,337 B2 | 8/2021 | Bohana-kashtan | |
| 2009/0306772 A1 | 12/2009 | Tao et al. | |
| 2013/0196369 A1 * | 8/2013 | Hikita | C12N 5/0621 |
| | | | 435/39 |
| 2018/0228846 A1 | 8/2018 | Bohana-kashtan | |

FOREIGN PATENT DOCUMENTS

| | | |
|---|---|---|
| CN | 103555654 A | 2/2014 |
| CN | 104946591 A | 9/2015 |
| EP | 2128244 A1 | 12/2009 |
| GB | 2327675 A | 2/1999 |
| JP | 2010524457 A | 7/2010 |
| WO | 01/55114 A1 | 8/2001 |
| WO | 02/060875 A1 | 8/2002 |
| WO | 03/068233 A1 | 8/2003 |
| WO | 2005014549 A1 | 2/2005 |
| WO | 2006040763 A2 | 4/2006 |
| WO | 2006070370 A2 | 7/2006 |
| WO | 2008129554 A1 | 10/2008 |
| WO | 2013114360 A1 | 8/2013 |
| WO | 2013184809 A1 | 12/2013 |
| WO | 2014087244 A2 | 6/2014 |

OTHER PUBLICATIONS

Rodin et al. Clonal culturing of human embryonic stem cells on laminin-521/E-cadherin matrix in defined and xeno-free environment. Nature Communications (Jan. 2014), 5, Article No. 3195, 13 pages. (Year: 2014).*

Pineda et al. Differentiation Patterns of Embryonic Stem Cells in Two- versus Three-Dimensional Culture. Cells Tissues Organs (2013), 197, 399-410. (Year: 2013).*

Sonoda et al. A protocol for the culture and differentiation of highly polarized human retinal pigment epithelial cells. Nature Protocols (2009), 4(5), 662-673. (Year: 2009).*

Tano et al. A Novel In Vitro Method for Detecting Undifferentiated Human Pluripotent Stem Cells as Impurities in Cell Therapy Products Using a Highly Efficient Culture System. PLoS One (Oct. 2014), 9(10), e110496, 11 pages. (Year: 2014).*

Maurotti et al. Small-molecule-directed, efficient generation of retinal pigment epithelium from human pluripotent stem cells. (PNAS (Sep. 1st, 2015), 112(35), 10950-10955 and appended Supporting Information. (Year: 2015).*

International Preliminary Report on Patentability issued in International Application No. PCT/IL16/51155, mailed on May 11, 2018, 8 pages.

International Search Report and Written Opinion issued in International Application No. PCT/IL16/51155, mailed on Dec. 19, 2016, 10 pages.

Algvere et al. (Mar. 1997), "Transplantation of RPE in Age-related Macular Degeneration: Observations in Disciform Lesions and Dry RPE Atrophy", Graefe's Archive for Clinical and Experimental Ophthalmology, 235(3):149-158.

Anni et al. (Jan. 20, 2014), "Structure and Barrier Properties of Human Embryonic Stem Cell-Derived Retinal Pigment Epithelial Cells Are Affected by Extracellular Matrix Protein Coating", Tissue Engineering Part A, 20(3-4):622-634.

Aoi et al. (Aug. 1, 2008), "Generation of Pluripotent Stem Cells from Adult Mouse Liver and Stomach Cells", Science, 321(5889):699-702.

Bigar et al. (Aug. 1992), "Corneal Transplantation", Current Opinion in Ophthalmology, 3(4):473-481.

Bongso et al. (Aug. 1989), "Improved Quality of Human Embryos when Co-Cultured with Human Ampullary Cells", Human Reproduction, 4(6):706-713.

Burdon et al. (1995), "A Survey of Corneal Graft Practice in the United Kingdom", Eye (Lond)., 9(Suppl.):6-12.

Chacko et al. (Feb. 24, 2000), "Survival and Differentiation of Cultured Retinal Progenitors Transplanted in the Subretinal Space of the Rat", Biochemical and Biophysical Research Communications, 268(3):842-846.

Chung et al. (Feb. 7, 2008), "Human Embryonic Stem Cell Lines Generated without Embryo Destruction", Cell Stem Cell, 2(2):113-117.

Doetschman et al. (May 1988), "Establishment of Hamster Blastocyst-Derived Embryonic Stem (ES) Cells", Developmental Biology, 127(1):224-227.

Gardner et al. (Jan. 1998), "Culture and Transfer of Human Blastocysts Increases Implantation Rates and Reduces the Need for Multiple Embryo Transfers", Fertility and Sterility, 69(1):84-88.

Giles et al. (Oct. 1993), "Pluripotency of Cultured Rabbit Inner Cell Mass Cells Detected by Isozyme Analysis and Eye Pigmentation of Fetuses Following Injection into Blastocysts or Morulae", Molecular Reproduction and Development, 36(2):130-138.

Graves et al. (Dec. 1993), "Derivation and Characterization of Putative Pluripotential Embryonic Stem Cells from Preimplantation Rabbit Embryos", Molecular Reproduction and Development, 36(4):424-433.

Iannaccone et al. (May 1994), "Pluripotent Embryonic Stem Cells from the Rat are Capable of Producing Chimeras", Developmental Biology, 163(1):288-292.

Kalkan et al. (Dec. 2014), "Mapping the Route From Naive Pluripotency to Lineage Specification", Philosophical Transactions of the Royal Society B Biological Sciences, 20130540, 369(1657):10 pages.

Mitalipova et al. (2001), "Pluripotency of Bovine Embryonic Cell Line Derived from Precompacting Embryos", Cloning, 3(2):59-67.

Notarianni et al. (1991), "Derivation of Pluripotent, Embryonic Cell Lines From the Pig and Sheep", Journal of Reproduction and fertility. Supplement, 43:255-260.

Oplinger et al. (Apr. 1998), "A Comparison of Corneal Autografts With Homografts", Ophthalmic Surgery, Lasers and Imaging Retina, 29(4):305-308.

Park et al. (Jan. 10, 2008), "Reprogramming of Human Somatic Cells to Pluripotency With Defined Factors", Nature, 451(7175):141-146.

Patel et al. (Apr. 2000), "Indications for and Outcomes of Repeat Penetrating Keratoplasty, 1989-1995", Ophthalmology, 107(4):719-724.

Peyman et al. (Feb. 1991), "A Technique for Retinal Pigment Epithelium Transplantation for Age-related Macular Degeneration Secondary to Extensive Subfoveal Scarring", Ophthalmic Surgery, Lasers and Imaging Retina, 22(2):102-108 (9 pages).

Reubinoff et al. (Apr. 2000), "Embryonic Stem Cell Lines From Human Blastocysts: Somatic Differentiation in Vitro", Nature Biotechnology, 18(4):399-404.

Shamblott et al. (Nov. 1998), "Derivation of Pluripotent Stem Cells from Cultured Human Primordial Germ Cells", Proceedings of the National Academy of Sciences of the United States of America, 95(23):13726-13731.

Sieving et al. (Mar. 7, 2006), "Ciliary Neurotrophic Factor (CNTF) for human retinal degeneration: Phase I Trial of CNTF Delivered by Encapsulated Cell Intraocular Implants", Proceedings of the National Academy of Sciences of the United States of America, 103(10):3896-3901.

Stern et al. (Aug. 1, 2015), "Retinal Pigment Epithelial Cell Proliferation", Experimental Biology and Medicine, 240(8):1079-1086.

Takahashi et al. (Nov. 30, 2007), "Induction of Pluripotent Stem Cells From Adult Human Fibroblasts by Defined Factors", Cell, 131(5):861-872.

Thomson et al. (Nov. 6, 1998), "Embryonic Stem Cell Lines Derived from Human Blastocysts", Science, 282(5391):1145-1147.

Thomson et al. (Aug. 1995), "Isolation of a Primate Embryonic Stem Cell Line", Proceedings of the National Academy of Sciences of the United States of America, 92(17):7844-7848.

Thomson et al. (Aug. 1996), "Pluripotent Cell Lines Derived from Common Marmoset (*Callithrix jacchus*) Blastocysts", Biology of Reproduction, 55(2):254-259.

(56) References Cited

OTHER PUBLICATIONS

Thomson et al. (1998), "Primate Embryonic Stem Cells", Current Topics in Developmental Biology, 38:133-165.
Tsubota Kazuo (Nov.-Dec. 1999), "Ocular Surface Management in Corneal Transplantation, A Review", Japanese Journal of Ophthalmology, 43(6):502-508.
Wheeler Matthew B. (1994), "Development and Validation of Swine Embryonic Stem Cells: A Review", Reproduction, Fertility and Development, 6(5):563-568.
Yamanaka Shinya (2007), "Strategies and New Developments in the Generation of Patient-specific Pluripotent Stem Cells", Cell Stem Cell, 1(1):39-49.
Haoqian et al. (2015) "Expression of Mitf and Pax6 Genes during the Differentiation of Mouse Embryonic Stem Cells Into Retinal Pigment Epithelial Cells", Journal of the Third Military Medical University, 37(9):827-832.
Leach et al. (2015) "Concise Review: Making Stem Cells Retinal: Methods for Deriving Retinal Pigment Epithelium and Implications for Patients With Ocular Disease", Stem Cells, 33(8):2363-2373.
Buchholz et al. (May 2013) "Rapid and Efficient Directed Differentiation of Human Pluripotent Stem Cells Into Retinal Pigmented Epithelium", Stem Cells Translational Medicine, 2(5):384-393.
Notice of Opposition received in European Patent Application No. 16795439.5, mailed on Jun. 2, 2022, 5 pages.

\* cited by examiner hESCs grown on hUCF in 4 Center Well Plates

Collagenase → hESCs Passaged onto laminin 521 coated T25 Flasks w/o hUCF

- Differentiation with Nicotinamide and Activin A
- Filtration
- Expansion

Cells at the end of P0

Tryple Select →

- Expansion in flasks

Cells at the end of P2

PREPARATION OF RETINAL PIGMENT EPITHELIUM CELLS

FIELD AND BACKGROUND OF THE INVENTION

The present invention, in some embodiments thereof, relates to methods of preparing retinal pigment epithelium cells from pluripotent stem cells.

The retinal pigmented epithelium (RPE) is a monolayer of pigmented cells, which lies between the neural retina and the choriocapillaris. The RPE cells play crucial roles in the maintenance and function of the retina and its photoreceptors. These include the formation of the blood-retinal barrier, absorption of stray light, supply of nutrients to the neural retina, regeneration of visual pigment, and uptake and recycling of shed outer segments of photoreceptors.

Retinal tissue may degenerate for a number of reasons. Among them are: artery or vein occlusion, diabetic retinopathy and retinopathy of prematurity, which are usually non-hereditary. There are hereditary diseases such as retinitis pigmentosa, retinoschisis, lattice degeneration, Best disease, Stargardt disease which also involve retinal tissue degeneration. A common retinal degeneration condition is age related macular degeneration (AMD). These conditions are characterized by progressive types of retinal degeneration.

RPE cells may potentially be used for cell replacement therapy of the degenerating RPE in retinal diseases mentioned above. It may be also used as a vehicle for the introduction of genes for the treatment of retinal degeneration diseases. These cells may also serve as an in vitro model of retinal degeneration diseases, as a tool for high throughput screening for a therapeutic effect of small molecules, and for the discovery and testing of new drugs for retinal degeneration diseases. RPE cells could also be used for basic research of RPE development, maturation, characteristics, properties, metabolism, immunogenicity, function and interaction with other cell types.

Human fetal and adult RPE has been used as an alternative donor source for allogeneic transplantation. However, practical problems in obtaining sufficient tissue supply and the ethical concerns regarding the use of tissues from aborted fetuses limit widespread use of these donor sources. Given these limitations in supply of adult and fetal RPE grafts, the potential of alternative donor sources have been studied. Human pluripotent stem cells provide significant advantages as a source of RPE cells for transplantation. Their pluripotent developmental potential may enable their differentiation into authentic functional RPE cells, and given their potential for infinite self renewal, they may serve as an unlimited donor source of RPE cells. Indeed, it has been demonstrated that human embryonic stem cells (hESCs) and human induced pluripotent stem cells (iPS) may differentiate into RPE cells in vitro, attenuate retinal degeneration and preserve visual function after subretinal transplantation to the Royal College of Surgeons (RCS) rat model of retinal degeneration that is caused by RPE dysfunction. Therefore, pluripotent stem cells may be an unlimited source for the production of RPE cells.

Current protocols for the derivation of RPE cells from pluripotent stem cells are labor intensive and time-consuming, yielding limited numbers of pigmented cells. New methods are required to produce RPE cells in quantities large enough that they can be used in the clinical setting.

Background art includes WO 2013/114360, WO 2008/129554 and WO 2013/184809.

SUMMARY OF THE INVENTION

According to an aspect of the present invention there is provided a method of generating retinal pigment epithelial (RPE) cells comprising:
(a) culturing a cell population of undifferentiated human pluripotent stem cells on an adherent surface in a medium comprising a differentiating agent to obtain differentiating cells, wherein at least 50% of the cells of the cell population are Oct4$^+$TRA-1-60$^+$; and
(b) culturing the differentiating cells on the adherent surface in a medium which comprises one or more members of the TGFβ superfamily to obtain RPE cells.

According to an aspect of the present invention there is provided a method of treating a retinal disease in a subject in need thereof comprising:
(a) generating RPE cells according to the method described herein; and
(b) transplanting a therapeutically effective amount of the RPE cells into the subject's eye following the harvesting, thereby treating the disease.

According to an aspect of the present invention there is provided a population of RPE cells generated according to the method described herein.

According to an aspect of the present invention there is provided a method of treating a retinal disease or disorder in a subject in need thereof comprising administering a therapeutically effective amount of the RPE cells described herein to the subject thereby treating the retinal disease or disorder.

According to some embodiments of the invention, the method further comprises expanding the population of undifferentiated human pluripotent stem cells on the adherent surface in the absence of the differentiating agent prior to step (a).

According to some embodiments of the invention, the expanding is effected in the absence of the differentiating agent.

According to some embodiments of the invention, the method further comprises isolating the RPE cells from the adherent surface following step (b).

According to some embodiments of the invention, the method further comprises culturing the RPE cells following the isolating on an additional adherent surface to generate an expanded population of RPE cells.

According to some embodiments of the invention, the method further comprises harvesting the RPE cells.

According to some embodiments of the invention, the isolating is effected enzymatically.

According to some embodiments of the invention, the method further comprises expanding the human pluripotent stem cells on human feeder cells prior to step (a).

According to some embodiments of the invention, the method further comprises expanding the human pluripotent stem cells on human feeder cells prior to the expanding on the adherent surface.

According to some embodiments of the invention, more than 90% of the cells of the expanded population of RPE cells are CRALBP$^+$PMEL17$^+$.

According to some embodiments of the invention, the adherent surface is selected from the group consisting of laminin, fibronectin, collagen I, vitronectin and collagen IV.

According to some embodiments of the invention, the adherent surface is laminin or vitronectin.

According to some embodiments of the invention, the laminin is human laminin.

According to some embodiments of the invention, the laminin is laminin 521.

According to some embodiments of the invention, the additional adherent surface is selected from the group consisting of gelatin, poly-d-lysine, laminin, collagen I and collagen IV.

According to some embodiments of the invention, the additional adherent surface is gelatin or poly-d-lysine.

According to some embodiments of the invention, the method is effected for at least 3 weeks.

According to some embodiments of the invention, the method further comprises cryopreserving the RPE cells following the harvesting.

According to some embodiments of the invention, the cryopreserving is effected in a medium selected from the group consisting of 90% HS/10% DMSO, CryoStor 2%, CryoStor 5% and CryoStor 10%, and Stem Cell Banker.

According to some embodiments of the invention, the human feeder cells comprise human cord fibroblasts.

According to some embodiments of the invention, the human pluripotent stem cells comprise human embryonic stem cells.

According to some embodiments of the invention, the differentiating agent comprises nicotinamide.

According to some embodiments of the invention, the medium of step (a) is devoid of activin A.

According to some embodiments of the invention, the member of the TGFβ superfamily is selected from the group consisting of TGFβ1, TGFβ3 and activin A.

According to some embodiments of the invention, the medium of step (b) comprises nicotinamide and activin A.

According to some embodiments of the invention, the method further comprises a step of culturing the RPE cells in a medium comprising nicotinamide and devoid of activin A following step (b).

According to some embodiments of the invention, the step (a) is effected for at least 5 days.

According to some embodiments of the invention, the step (b) is effected for at least one week.

According to some embodiments of the invention, the transplanting of the differentiated RPE cells is effected at the subretinal space of the eye.

According to some embodiments of the invention, the RPE cells are transplanted in a suspension, or as a monolayer of cells immobilized on a matrix or a substrate.

According to some embodiments of the invention, the retinal disease or disorder is selected from at least one of retinitis pigmentosa, lebers congenital amaurosis, hereditary or acquired macular degeneration, age related macular degeneration (AMD), Best disease, retinal detachment, gyrate atrophy, choroideremia, pattern dystrophy, RPE dystrophies, Stargardt disease, RPE and retinal damage due to damage caused by any one of photic, laser, inflammatory, infectious, radiation, neovascular or traumatic injury.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-D are graphs illustrating the purity of hESC derived pigmented cells generated without SBs at the end of P2 post cryopreservation (FIGS. 4C-D) as compared to non-differentiated embryonic stem cells (negative control; FIG. 4A) and RPE cells generated through SBs and the action of Activin A and nicotinamide (positive control; FIG. 4B).

FIG. 5A—RPE cells at passage 1 (X10); FIG. 5B—RPE cells at passage 2 (X10). FIG. 5C—RPE cells at passage 2 (X20).

FIG. 6A—Anti Bestrophin (nuclei counter staining with DAPI). FIG. 6B—Anti CRALBP (nuclei counter staining with DAPI). FIG. 6C—Anti MITF. FIG. 6D—Anti PEDF (nuclei counter staining with DAPI). FIG. 6E—Anti ZO-1.

DESCRIPTION OF SPECIFIC EMBODIMENTS OF THE INVENTION

The present invention, in some embodiments thereof, relates to methods of preparing retinal pigment epithelium cells from pluripotent stem cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Human embryonic stem cells have been proposed as a cellular source for the generation of RPE cells. Two general approaches have been used to obtain retinal pigment epithelium (RPE) cells from hESCs, spontaneous differentiation and directed differentiation.

In spontaneous differentiation, hESCs in flat colonies or in embryoid bodies (EBs) are allowed to spontaneously differentiate into a population of cells containing pigmented RPE cells.

Directed differentiation of human embryonic stem cells (hESCs) to RPE cells is traditionally performed following generation of embryoid/spheroid bodies (SBs)—see for example U.S. Pat. No. 8,956,866, the contents of which are incorporated herein by reference. However, this step is variable in nature which hampers upscale needed for a commercial process.

Figure 2B:
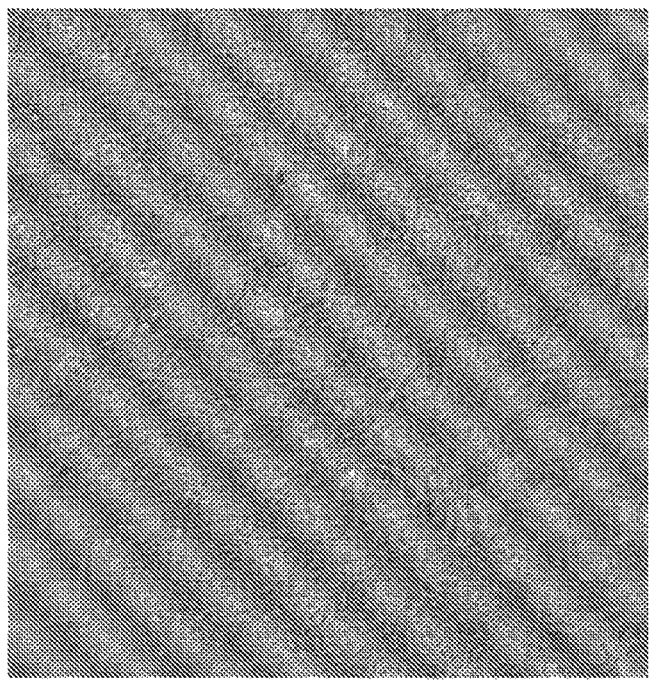
FIGS. 2A-B are photographs depicting the RPE cells at the end of the differentiation phase (FIG. 2A) and at the end of P0 phase (FIG. 2B).
Figure 2A:
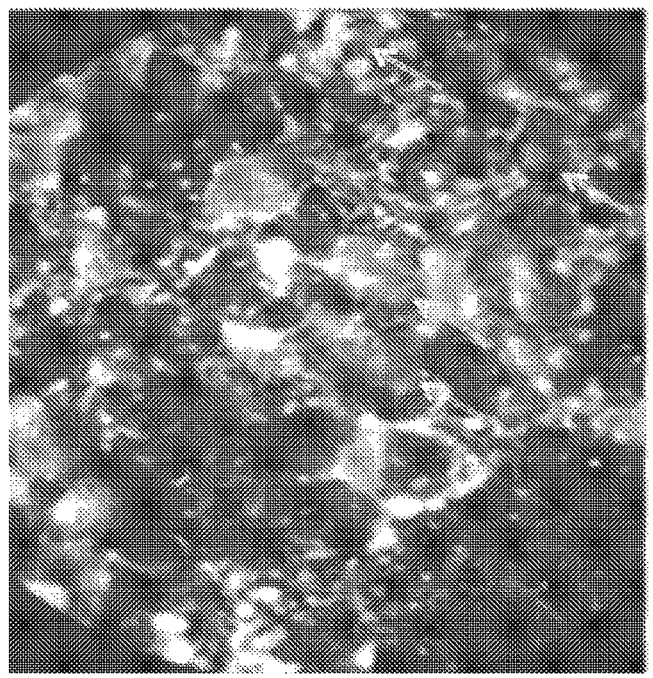

The present inventors now propose that RPE cells may be generated without initial differentiation as embryoid bodies or spheroid bodies. This was demonstrated by identification of the typical polygonal morphology of RPE cells following a directed differentiation protocol carried out entirely under adherent conditions (FIGS. 2A-B).

FACs analysis, performed following expansion of enzymatically isolated cells, demonstrated that more than 99% of the cells were CRALBP$^+$PMEL17$^+$ (FIGS. 3A-C) indicating that the process generates highly purified populations of RPE cells.

Thus, according to a first aspect of the present invention there is provided a method of generating retinal pigment epithelial (RPE) cells comprising:

(a) culturing a cell population of undifferentiated human pluripotent stem cells on an adherent surface in a medium comprising a differentiating agent to obtain differentiating cells, wherein at least 50% of the cells of the cell population are Oct4$^+$TRA-1-60$^+$; and (b) culturing the differentiating cells on the adherent surface in a medium which comprises one or more members of the TGFβ superfamily to obtain RPE cells.

"Retinal pigment epithelium cells", "RPE cells", "RPEs", which may be used interchangeably as the context allows, refers to cells of a cell type functionally similar to that of native RPE cells which form the pigment epithelium cell layer of the retina (e.g. upon transplantation within an eye, they exhibit functional activities similar to those of native RPE cells).

According to one embodiment, RPE cells express at least one, two, three, four or five markers of mature RPE cells. Such markers include, but are not limited to CRALBP, RPE65, PEDF, PMEL17, Bestrophin and tyrosinase. Optionally, RPE cells may also express a marker of an RPE progenitor—e.g. MITF. In another embodiment, the RPE cells express PAX-6.

As used herein the phrase "markers of mature RPE cells" refers to antigens (e.g. proteins) that are elevated (e.g. at least 2 fold, at least 5 fold, at least 10 fold) in mature RPE cells with respect to non RPE cells or immature RPE cells.

As used herein the phrase "markers of RPE progenitor cells" refers to antigens (e.g. proteins) that are elevated (e.g. at least 2 fold, at least 5 fold, at least 10 fold) in RPE progenitor cells with respect to non RPE cells.

According to another embodiment, the RPE cells have a morphology similar to that of native RPE cells which form the pigment epithelium cell layer of the retina i.e. pigmented and having a characteristic polygonal shape.

According to still another embodiment, the RPE cells are capable of treating diseases such as macular degeneration.

According to still another embodiment, the RPE cells fulfill at least 1, 2, 3, 4 or all of the requirements listed herein above.

As used herein, the phrase "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). Preferably, the phrase "stem cells" encompasses embryonic stem cells (ESCs), induced pluripotent stem cells (iPSCs), adult stem cells, mesenchymal stem cells and hematopoietic stem cells.

According to a particular embodiment, the RPE cells are generated from pluripotent stem cells. Such cells are capable of differentiating into any of the three germ layers: endoderm (interior stomach lining, gastrointestinal tract, the lungs), mesoderm (muscle, bone, blood, urogenital), or ectoderm (epidermal tissues and nervous system). According to a particular embodiment the pluripotent stem cell is capable of differentiating into every cell of the embryo proper, e.g., embyronic stem cells and iPSCs (e.g. ESCs or iPSCs).

Induced pluripotent stem cells (iPSCs) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); I H Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation. The embryonic stem cells of some embodiments of the invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by a procedure in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Reubinoff et al Nat Biotechnol 2000, May: 18(5): 559; Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used according to some embodiments of the invention Human ES cells can be purchased from the NIH human embryonic stem cells registry [www.grants (dot) nih (dot) gov/stem_cells/registry/current (dot) htm]. Non-limiting examples of commercially available embryonic stem cell lines are HAD-C102, ESI, BG01, BG02, BG03, BG04, CY12, CY30, CY92, CY10, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WA01, UCSF4, NYUES1, NYUES2, NYUES3, NYUES4, NYUES5, NYUES6, NYUES7, UCLA 1, UCLA 2, UCLA 3, WA077 (H7), WA09 (H9), WA13 (H13), WA14 (H14), HUES 62, HUES 63, HUES 64, CT1, CT2, CT3, CT4, MA135, Eneavour-2, WIBR1, WIBR2, WIBR3, WIBR4, WIBR5, WIBR6, HUES 45, Shef 3, Shef 6, BJNhem19, BJNhem20, SA001, SA001.

According to a specific embodiment, the embryonic stem cell line is HAD-C102 or ESI.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Yet another method for preparing ES cells is by parthenogenesis. The embryo is also not destroyed in the process.

Currently practiced ES culturing methods are mainly based on the use of feeder cell layers which secrete factors needed for stem cell proliferation, while at the same time, inhibit their differentiation. The culturing is typically effected on a solid surface—e.g. a surface coated with gelatin or vimentin. Exemplary feeder layers include Human embryonic fibroblasts, adult fallopian epithelial cells, primary mouse embryonic fibroblasts (PMEF), mouse embryonic fibroblasts (MEF), murine fetal fibroblasts (MFF), human embryonic fibroblast (HEF), human fibroblasts obtained from the differentiation of human embryonic stem cells, human fetal muscle cells (HFM), human fetal skin cells (HFS), human adult skin cells, human foreskin fibroblasts (HFF), human umbilical cord fibroblasts, human cells obtained from the umbilical cord or placenta, and human marrow stromal cells (hMSCs). Growth factors may be added to the medium to maintain the ESCs in an undifferentiated state. Such growth factors include bFGF and/or TGFβ. In another embodiment, agents may be added to the medium to maintain the hESCs in a naïve undifferentiated state—see for example Kalkan et al, 2014, Phil. Trans. R. Soc. B, 369: 20130540.

Feeder cell free systems have also been used in ES cell culturing, such systems utilize matrices supplemented with serum replacement, cytokines and growth factors (including IL6 and soluble IL6 receptor chimera) as a replacement for the feeder cell layer. Stem cells can be grown on a solid surface such as an extracellular matrix (e.g., Matrigel®, laminin or vitronectin) in the presence of a culture medium—for example the Lonza L7 system, mTeSR, StemPro, XFKSR, E8, Nutristem). Unlike feeder-based cultures which require the simultaneous growth of feeder cells and stem cells and which may result in mixed cell populations, stem cells grown on feeder-free systems are easily separated from the surface. The culture medium used for growing the stem cells contains factors that effectively inhibit differentiation and promote their growth such as MEF-conditioned medium and bFGF.

Following optional expansion, the pluripotent ESCs are subjected to directed differentiation on an adherent surface (without intermediate generation of spheroid or embryoid bodies).

Thus, according to this aspect of the present invention at least 50%, 55%, 60%, 65%, 70%, 75%, 80%, 85%, 90%, 91%, 92%, 93%, 94%, 95%, 96%, 97%, 98%, 99% or 100% of the cells which are subjected to directed differentiation on the adherent surface are undifferentiated ESCs and express markers of pluripotency. For example at least 50%, 55%, 60%, 65%, 70%, 75%, 80%, 85%, 90%, 91%, 92%, 93%, 94%, 95%, 96%, 97%, 98%, 99% or 100% of the cells are Oct4$^+$TRA-1-60$^+$. The non-differentiated ESCs preferably express other markers of pluripotency such as NANOG, Rex-1, alkaline phosphatase, Sox2, TDGF-beta, SSEA-3, SSEA-4 and/or TRA-1-81.

In one exemplary differentiation protocol, the non-differentiated embryonic stem cells are differentiated towards the RPE cell lineage on an adherent surface using a first differentiating agent and then further differentiated towards RPE cells using a member of the transforming growth factor-β (TGFβ) superfamily, (e.g. TGFβ1, TGFβ2, and TGFβ3 subtypes, as well as homologous ligands including activin (e.g., activin A, activin B, and activin AB), nodal, anti-mullerian hormone (AMH), some bone morphogenetic proteins (BMP), e.g. BMP2, BMP3, BMP4, BMP5, BMP6, and BMP7, and growth and differentiation factors (GDF)). According to a specific embodiment, the member of the transforming growth factor-β (TGFβ) superfamily is activin A—e.g. between 20-200 ng/ml e.g. 100-180 ng/ml.

According to a particular embodiment, the first differentiating agent is nicotinamide (NA)—e.g. between 1-100 mM, 5-50 mM, 5-20 mM, e.g. 10 mM.

According to another embodiment, the first differentiating agent is 3-aminobenzamide.

NA, also known as "niacinamide", is the amide derivative form of Vitamin B3 (niacin) which is thought to preserve and improve beta cell function. NA has the chemical formula $C_6H_6N_2O$. NA is essential for growth and the conversion of foods to energy, and it has been used in arthritis treatment and diabetes treatment and prevention.

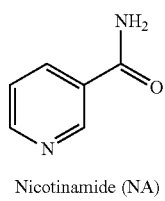

Nicotinamide (NA)

According to a particular embodiment, the nicotinamide is a nicotinamide derivative or a nicotinamide mimic. The term "derivative of nicotinamide (NA)" as used herein denotes a compound which is a chemically modified derivative of the natural NA. In one embodiment, the chemical modification may be a substitution of the pyridine ring of the basic NA structure (via the carbon or nitrogen member of the ring), via the nitrogen or the oxygen atoms of the amide moiety. When substituted, one or more hydrogen atoms may be replaced by a substituent and/or a substituent may be attached to a N atom to form a tetravalent positively charged nitrogen. Thus, the nicotinamide of the present invention includes a substituted or non-substituted nicotinamide. In another embodiment, the chemical modification may be a deletion or replacement of a single group, e.g. to form a thiobenzamide analog of NA, all of which being as appreciated by those versed in organic chemistry. The derivative in the context of the invention also includes the nucleoside derivative of NA (e.g. nicotinamide adenine). A variety of derivatives of NA are described, some also in connection with an inhibitory activity of the PDE4 enzyme (WO03/068233; WO02/060875; GB2327675A), or as VEGF-receptor tyrosine kinase inhibitors (WO01/55114). For example, the process of preparing 4-aryl-nicotinamide derivatives (WO05/014549). Other exemplary nicotinamide derivatives are disclosed in WO01/55114 and EP2128244.

Nicotinamide mimics include modified forms of nicotinamide, and chemical analogs of nicotinamide which recapitulate the effects of nicotinamide in the differentiation and maturation of RPE cells from pluripotent cells. Exemplary nicotinamide mimics include benzoic acid, 3-aminobenzoic acid, and 6-aminonicotinamide. Another class of compounds that may act as nicotinamide mimics are inhibitors of poly(ADP-ribose) polymerase (PARP). Exemplary PARP inhibitors include 3-aminobenzamide, Iniparib (BSI 201), Olaparib (AZD-2281), Rucaparib (AG014699, PF-01367338), Veliparib (ABT-888), CEP 9722, MK 4827, and BMN-673.

According to a particular embodiment, the differentiation is effected as follows:
a) culture of ESCs in a medium comprising a first differentiating agent (e.g. nicotinamide); and
b) culture of cells obtained from step a) in a medium comprising a member of the TGFβ superfamily (e.g. activin A) and the first differentiating agent (e.g. nicotinamide).

Preferably step (a) is effected in the absence of the member of the TGFβ superfamily.

The above described protocol may be continued by culturing the cells obtained in step b) in a medium comprising the first differentiating agent (e.g. nicotinamide), but devoid of a member of the TGFβ superfamily (e.g. activin A). This step is referred to herein as step (b*).

The above described protocol is now described in further detail, with additional embodiments.

Step (a): The process is started once sufficient quantities of ESCs are obtained (e.g. following expansion on feeders). They are typically removed from the feeder culture (e.g. by using collagenase A, dispase, TrypLE select, EDTA) and plated onto a feeder-free adherent substrate (e.g. laminin, vitronectin, fibronectin, collagen I and collagen IV). According to a particular embodiment, the feeder-free adherent substrate is laminin—for example laminin 521 or vitronectin (e.g. Millipore CC080 Lot LV1689930). The non-differentiated embryonic stem cells may be further expanded for 1-10 days on the adherent substrate, or may be passaged and expanded for longer periods (above 10 days) prior to the initiation of directed differentiation in a medium that prevents differentiation (e.g. a medium which contains bFGF and TGFβ). Directed differentiation is then initiated by replacing the medium with one that comprises the first differentiation agent (e.g. nicotinamide). The medium does not comprise members of the TGFβ superfamily (activin A, bFGF and TGFβ) at levels that are used for the second differentiation step. In one embodiment, the medium is completely devoid of a member of the TGFβ superfamily. In another embodiment, the level of TGFβ superfamily member in the medium is less than 20 ng/ml, 10 ng/ml, 1 ng/ml or even less than 0.1 ng/ml.

Exemplary concentrations of nicotinamide are between 1-100 mM, 5-50 mM, 5-20 mM, e.g. 10 mM.

This stage may be effected for a minimum of 1 day, more preferably two days, three days, 1 week or even 14 days. Preferably, the cells are not cultured at this stage for more than 3 weeks in the presence of nicotinamide (and in the absence of activin).

According to one embodiment, when the cells are cultured on the adherent substrate e.g. laminin, vitronectin the atmospheric oxygen conditions are 20%. They may be manipulated such that the percentage is less than about 20%, 15%, 10%, more preferably less than about 9%, less than about 8%, less than about 7%, less than about 6% and more preferably about 5% (e.g. between 1%-20%, 1%-10% or 0-5%).

According to a particular embodiment, the cells are cultured on the adherent substrate initially under normal atmospheric oxygen conditions and then lowered to less than normal atmospheric oxygen conditions.

Preferably, once the non-differentiated ESCs are plated on the adherent substrate, they are not removed until pigmented cells are observed.

Step (b): Following the first stage of directed differentiation, (step a; i.e. culture in the presence of nicotinamide (e.g. between 1-100 mM, 5-50 mM, 5-20 mM, e.g. 10 mM), semi-differentiated cells are obtained. Such semi-differentiated cells (also referred to herein, as differentiating cells), are differentiated along the retinal pigment epithelium pathway. Such cells may express markers of neural progenitor cells, or early markers of RPE cells.

The differentiating cells are then subjected to a further stage of differentiation on the adherent substrate—culturing in the presence of nicotinamide (e.g. between 1-100 mM, 5-50 mM, 5-20 mM, e.g. 10 mM) and activin A (e.g. 20-200 ng/ml or 100-200 ng/ml—for example 140 ng/ml, 150 ng/ml, 160 ng/ml or 180 ng/ml). This stage may be effected for 1 day to 10 weeks, 3 days to 10 weeks, 1 week to 10 weeks, one week to eight weeks, one week to four weeks, for example for at least one day, at least two days, at least three days, at least 5 days, at least one week, at least two weeks, at least three weeks, at least four weeks, at least five weeks, at least six weeks, at least seven weeks, at least eight weeks, at least nine weeks, at least ten weeks.

According to a specific embodiment this stage is effected for about two weeks. This stage of differentiation may be effected at low or normal atmospheric oxygen conditions, as detailed herein above.

Step (b*): Following the second stage of directed differentiation (i.e. culture in the presence of nicotinamide and activin A on an adherent substrate; step (b)), the further differentiated cells are optionally subjected to a subsequent stage of differentiation on the adherent substrate—culturing in the presence of nicotinamide (e.g. between 1-100 mM, 5-50 mM, 5-20 mM, e.g. 10 mM), in the absence of the member of the TGFB superfamily e.g. activin A.

In one embodiment, this medium is completely devoid of a member of the TGFβ superfamily. In another embodiment, the level of TGFβ superfamily in the medium is less than 20 ng/ml, 10 ng/ml, 1 ng/ml or even less than 0.1 ng/ml.

This stage may be effected for at least one day, 2, days, 5 days, at least one week, at least two weeks, at least three weeks or even four weeks. Preferably this stage is effected for about one week. This stage of differentiation may also be carried out at low or normal atmospheric oxygen conditions, as detailed herein above.

The differentiation process is typically carried out until at least 1%, 5%, 10%, 15%, 20%, 25%, 30%, 35%, 40%, 45%, 50%, 55%, 6%, 65%, 70%, 75%, 80%, 85%, 90%, 95% of the cells on the plate are pigmented cells.

The basic medium in which the ESCs are differentiated is any known cell culture medium known in the art for supporting cells growth in vitro, typically, a medium comprising a defined base solution, which includes salts, sugars, amino acids and any other nutrients required for the maintenance of the cells in the culture in a viable state. According to a specific embodiment, the basic medium is not a conditioned medium. Non-limiting examples of commercially available basic media that may be utilized in accordance with the invention comprise Nutristem (without bFGF and TGFβ for ESC differentiation, with bFGF and TGFβ for ESC expansion) Neurobasal™ KnockOut SR XenoFree Medium, KO-DMEM, DMEM, DMEM/F12, Cellgro™ Stem Cell Growth Medium, or X-Vivo™. The basic medium may be supplemented with a variety of agents as known in the art dealing with cell cultures. The following is a non-limiting reference to various supplements that may be included in the culture system to be used in accordance with the present disclosure:
  serum or with a serum replacement containing medium, such as, without being limited thereto, knock out serum replacement (KOSR), Nutridoma-CS, TCH™, N2, N2 derivative, or B27 or a combination;
  an extracellular matrix (ECM) component, such as, without being limited thereto, fibronectin, laminin, collagen and gelatin. The ECM may them be used to carry the one or more members of the TGFβ superfamily of growth factors;
  an antibacterial agent, such as, without being limited thereto, penicillin and streptomycin; and
  non-essential amino acids (NEAA),
  neurotrophins which are known to play a role in promoting the survival of SCs in culture, such as, without being limited thereto, BDNF, NT3, NT4.

According to a preferred embodiment, the medium used for differentiating the ESCs is Nutristem medium (Biological Industries, 05-102-1A or 05-100-1A).

According to a particular embodiment differentiation of ESCs is effected under xeno free conditions.

According to one embodiment, the proliferation/growth medium is devoid of xeno contaminants i.e. free of animal derived components such as serum, animal derived growth factors and albumin. Thus, according to this embodiment, the culturing is performed in the absence of xeno contaminants.

Other methods for culturing ESCs under xeno free conditions are provided in U.S. Patent Application No. 20130196369, the contents of which are incorporated in their entirety.

The preparations comprising RPE cells may be prepared in accordance with Good Manufacturing Practices (GMP) (e.g., the preparations are GMP-compliant) and/or current Good Tissue Practices (GTP) (e.g., the preparations may be GTP-compliant).

During differentiation steps, the embryonic stem cells may be monitored for their differentiation state. Cell differentiation can be determined upon examination of cell or tissue-specific markers which are known to be indicative of differentiation.

Tissue/cell specific markers can be detected using immunological techniques well known in the art [Thomson J A et al., (1998). Science 282: 1145-7]. Examples include, but are not limited to, flow cytometry for membrane-bound or intracellular markers, immunohistochemistry for extracellular and intracellular markers and enzymatic immunoassay, for secreted molecular markers.

Following the stages of differentiation described herein above, a mixed cell population is obtained comprising both pigmented and non-pigmented cells.

According to one embodiment of this aspect of the present invention, all the cells of the mixed cell population are removed from the plate.

This may be effected enzymatically (e.g. using trypsin, (TrypLE Select)). According to this aspect of the present invention, at least 10%, 20%, 30%, at least 40%, at least 50%, at least 60%, at least 70% of the cells which are removed from the culture system (and subsequently expanded) are non-pigmented cells. In one embodiment, after all the cells are removed from the plate (e.g. enzymatically), they are purified (for example by using a strainer, such as a 40 μm strainer) and only subsequently expanded.

Furthermore, at least 10%, 20% or even 30% of the cells which are removed from the culture system (and subsequently expanded) are pigmented cells.

Preferably, at least 50%, 60%, 70%, 80%, 90%, 95%, 100% of all the cells in the culture system are removed (and subsequently expanded).

According to another embodiment, the non-pigmented cells are initially isolated and removed from the culture plate mechanically and subsequently the pigmented cells are removed.

The cells may be subjected to a filtering process prior to expansion and following harvesting of the cells. Thus for example, the cells may be filtered through a 10-100 μm strainer (e.g. a 40 μm strainer).

Expansion of the RPE cells may be effected on an extra cellular matrix, e.g. gelatin, collagen I, collagen IV, laminin and poly-D-lysine. For expansion, the cells may be cultured in serum-free KOM, serum comprising medium (e.g. DMEM+20%) or Nutristem medium (06-5102-01-1A Biological Industries). Under these culture conditions, after passaging under suitable conditions, the ratio of pigmented cells:non-pigmented cells increases such that a population of purified RPE cells is obtained. Such cells show the characteristic polygonal shape morphology and pigmentation of RPE cells.

The RPE cells may be expanded in suspension (with or without a micro-carrier) or in a monolayer. The expansion of the mixed population of cells in monolayer cultures or in suspension culture may be modified to large scale expansion in bioreactors by methods well known to those versed in the art.

According to one embodiment, the expansion phase is effected for at least one week, at least 2 weeks, at least 3 weeks, at least 4 weeks, at least 5 weeks, at least 6 weeks, at least 7 weeks, at least 8 weeks, at least 9 weeks or even 10 weeks. Preferably, the expansion phase is effected for 1 week-10 weeks, more preferably 2 weeks-10 weeks, more preferably, 3 weeks-10 weeks, more preferably 4 weeks-10 weeks, or 4 weeks-8 weeks.

According to still another embodiment, the RPE cells are passaged at least 1 time during the expansion phase, at least twice during the expansion phase, at least three times during the expansion phase, at least four times during the expansion phase or at least five times during the expansion phase.

The population of RPE cells generated according to the methods described herein may be characterized according to a number of different parameters.

Thus, for example, the RPE cells obtained may be polygonal in shape and pigmented.

Harvesting of the expanded population of RPE cells may be effected using methods known in the art (e.g. using an enzyme such as trypsin).

Following harvesting, the expanded population of RPE cells may optionally be cryopreserved using methods known in the art. Examples of media suitable for cryopreservation include but are not limited to 90% Human Serum/10% DMSO, CryoStor 10%, 5% and 2%, Stem Cell banker and Prime XV® FreezIS.

It will be appreciated that the cell populations disclosed herein are devoid of undifferentiated human embryonic stem cells. According to one embodiment, less than 1:250,000 cells are Oct4$^+$TRA-1-60$^+$ cells, as measured for example by FACS. The cells also have down regulated (by more than 5,000 fold) expression of GDF3 or TDGF as measured by PCR.

The RPE cells of this aspect of the present invention do not express other embryonic stem cell markers. Said one or more embryonic stem cell markers may comprise OCT-4, NANOG, Rex-1, alkaline phosphatase, Sox2, TDGF-beta, SSEA-3, SSEA-4, TRA-1-60, and/or TRA-1-81.

The RPE preparations may be substantially purified, with respect to non-RPE cells, comprising at least about 75%, 80%, 85%, 90%, 91%, 92%, 93%, 94%, 95%, 96%, 97%, 98%, 99%, or 100% RPE cells. The RPE cell preparation may be essentially free of non-RPE cells or consist of RPE cells. For example, the substantially purified preparation of RPE cells may comprise less than about 25%, 20%, 15%, 10%, 9%, 8%, 7%, 6%, 5%, 4%, 3%, 2%, or 1% non-RPE cell type. For example, the RPE cell preparation may comprise less than about 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% non-RPE cells.

The RPE cell preparations may be substantially pure, both with respect to non-RPE cells and with respect to RPE cells of other levels of maturity. The preparations may be substantially purified, with respect to non-RPE cells, and enriched for mature RPE cells. For example, in RPE cell preparations enriched for mature RPE cells, at least about 30%, 40%, 45%, 50%, 55%, 60%, 65%, 70%, 75%, 80%, 85%, 90%, 91%, 92%, 93%, 94%, 95%, 96%, 97%, 98%, 99%, 99%, or 100% of the RPE cells are mature RPE cells. The preparations may be substantially purified, with respect to non-RPE cells, and enriched for differentiated RPE cells rather than mature RPE cells. For example, at least about 30%, 40%, 45%, 50%, 55%, 60%, 65%, 70%, 75%, 80%, 85%, 90%, 91%, 92%, 93%, 94%, 95%, 96%, 97%, 98%, 99%, or 100% of the RPE cells may be differentiated RPE cells rather than mature RPE cells.

The preparations described herein may be substantially free of bacterial, viral, or fungal contamination or infection, including but not limited to the presence of HIV 1, HIV 2, HBV, HCV, HAV, CMV, HTLV 1, HTLV 2, parvovirus B19, Epstein-Barr virus, or herpesvirus 1 and 2, SV40, HHV5, 6, 7, 8, CMV, polyoma virus, HPV, Enterovirus. The preparations described herein may be substantially free of mycoplasma contamination or infection.

Another way of characterizing the cell populations disclosed herein is by marker expression. Thus, for example, at least 80%, 85%, 90%, 95% or 100% of the cells express Bestrophin 1, as measured by immunostaining. According to one embodiment, between 85-100% of the cells express bestrophin.

According to another embodiment, at least 80%, 85%, 87%, 89%, 90%, 95%, 97% or 100% of the cells express Microphthalmia-associated transcription factor (MITF), as measured by immunostaining. For example, between 85-100% of the cells express MITF.

According to another embodiment, at least 80% 85%, 87%, 89%, 90%, 95%, 97% or 100% of the cells express paired box gene 6 (PAX-6) as measured by immunostaining or FACS.

According to another embodiment, at least 80%, 85%, 87%, 89%, 90%, 95%, 97% or 100% of the cells express cellular retinaldehyde binding protein (CRALBP), as measured by immunostaining. For example, between 85-100% of the cells express CRALBP.

According to another embodiment, at least 80%, 85%, 87%, 89%, 90%, 95%, 97% or 100% of the cells express retinal pigment epithelium-specific protein 65 kDa (RPE65), as measured by immunostaining. For example, between 85-100% of the cells express RPE65.

The RPE cells express typically co-express markers indicative of terminal differentiation, e.g. bestrophin 1, premelanosome protein (PMEL17), CRALBP and/or RPE65.

Following the expansion phase cell populations comprising RPE cells are obtained whereby at least 70%, 71%, 72%, 73%, 74%, 75%, 76%, 77%, 78%, 79, 80%, 81%, 82%, 83%, 84%, 85%, 86%, 87%, 88%, 89, 90%, 91%, 92%, 93%, 94%, 95%, 96%, 97%, 98%, 99 or even 100% thereof are CRALBP$^+$PMEL17$^+$.

It would be well appreciated by those versed in the art that the derivation of RPE cells is of great benefit. They may be used as an in vitro model for the development of new drugs to promote their survival, regeneration and function. RPE cells may serve for high throughput screening for compounds that have a toxic or regenerative effect on RPE cells. They may be used to uncover mechanisms, new genes, soluble or membrane-bound factors that are important for the development, differentiation, maintenance, survival and function of photoreceptor cells.

The RPE cells may also serve as an unlimited source of RPE cells for transplantation, replenishment and support of malfunctioning or degenerated RPE cells in retinal degenerations. Furthermore, genetically modified RPE cells may serve as a vector to carry and express genes in the eye and retina after transplantation.

Eye conditions for which the RPE cells may serve as therapeutics include, but are not limited to retinal diseases or disorders generally associated with retinal dysfunction, retinal injury, and/or loss of retinal pigment epithelium. A non-limiting list of conditions which may be treated in accordance with the invention comprises retinitis pigmentosa, lebers congenital amaurosis, hereditary or acquired macular degeneration, age related macular degeneration (AMD), dry AMD, Best disease, retinal detachment, gyrate atrophy, choroideremia, pattern dystrophy as well as other dystrophies of the RPE, Stargardt disease, RPE and retinal damage due to damage caused by any one of photic, laser, inflammatory, infectious, radiation, neo vascular or traumatic injury.

Subjects which may be treated include primate (including humans), canine, feline, ungulate (e.g., equine, bovine, swine (e.g., pig)), avian, and other subjects. Humans and non-human animals having commercial importance (e.g., livestock and domesticated animals) are of particular interest. Exemplary mammals which may be treated include, canines; felines; equines; bovines; ovines; rodentia, etc. and primates, particularly humans. Non-human animal models, particularly mammals, e.g. primate, murine, lagomorpha, etc. may be used for experimental investigations.

The RPE cells generated as described herein may be transplanted to various target sites within a subject's eye. In accordance with one embodiment, the transplantation of the RPE cells is to the subretinal space of the eye, which is the normal anatomical location of the RPE (between the photoreceptor outer segments and the choroids). In addition, dependent upon migratory ability and/or positive paracrine effects of the cells, transplantation into additional ocular compartments can be considered including the vitreal space, inner or outer retina, the retinal periphery and within the choroids.

The number of viable cells that may be administered to the subject may be between 50,000-5×10$^6$ per injection or between 50,000-500,000.

The cells are typically formulated in a carrier (e.g. an isotonic solution and/or a saline) such as BSS Plus™. The carrier may optionally comprise additional factors that support RPE engraftment, integration, survival, potency etc.

The transplantation may be performed by various techniques known in the art. Methods for performing RPE transplants are described in, for example, U.S. Pat. Nos. 5,962,027, 6,045,791, and 5,941,250 and in Eye Graefes Arch Clin Exp Opthalmol March 1997; 235(3):149-58; Biochem Biophys Res Commun Feb. 24, 2000; 268(3): 842-6; Opthalmic Surg February 1991; 22(2): 102-8. Methods for performing corneal transplants are described in, for example, U.S. Pat. No. 5,755,785, and in Eye 1995; 9 (Pt 6 Su):6-12; Curr Opin Opthalmol August 1992; 3 (4): 473-81; Ophthalmic Surg Lasers April 1998; 29 (4): 305-8; Ophthalmology April 2000; 107 (4): 719-24; and Jpn J Ophthalmol November-December 1999; 43(6): 502-8. If mainly paracrine effects are to be utilized, cells may also be delivered and maintained in the eye encapsulated within a semi-permeable container, which will also decrease exposure of the cells to the host immune system (Neurotech USA CNTF delivery system; PNAS Mar. 7, 2006 vol. 103(10) 3896-3901).

The step of administering may comprise intraocular administration of the RPE cells into an eye in need thereof. The intraocular administration may comprise injection of the RPE cells into the subretinal space.

In accordance with one embodiment, transplantation is performed via pars plana vitrectomy surgery followed by delivery of the cells through a small retinal opening into the sub-retinal space or by direct injection.

The RPE cells may be transplanted in various forms. For example, the RPE cells may be introduced into the target site in the form of cell suspension, with matrix or adhered onto a matrix or a membrane, extracellular matrix or substrate such as a biodegradable polymer or a combination. The RPE cells may also be transplanted together (co-transplantation) with other retinal cells, such as with photoreceptors.

The effectiveness of treatment may be assessed by different measures of visual and ocular function and structure, including, among others, best corrected visual acuity (BCVA), retinal sensitivity to light as measured by perimetry or microperimetry in the dark and light-adapted states, full-field, multi-focal, focal or pattern electroretinography ERG), contrast sensitivity, reading speed, color vision, clinical biomicroscopic examination, fundus photography, optical coherence tomography (OCT), fundus auto-fluorescence (FAF), infrared and multicolor imaging, fluorescein or ICG angiography, and additional means used to evaluate visual function and ocular structure.

The subject may be administered corticosteroids prior to or concurrently with the administration of the RPE cells, such as prednisolone or methylprednisolone, Predforte.

According to another embodiment, the subject is not administered corticosteroids prior to or concurrently with the administration of the RPE cells, such as prednisolone or methylprednisolone, Predforte.

Immunosuppressive drugs may be administered to the subject prior to, concurrently with and/or following treatment.

The immunosuppressive drug may belong to the following classes:

Glucocorticoids, Cytostatics (e.g. alkylating agent or antimetabolite), antibodies (polyclonal or monoclonal), drugs acting on immunophilins (e.g. ciclosporin, Tacrolimus or Sirolimus). Additional drugs include interferons, opioids, TNF binding proteins, mycophenolate and small biological agents.

Examples of immunosuppressive drugs include: mesenchymal stem cells, anti-lymphocyte globulin (ALG) polyclonal antibody, anti-thymocyte globulin (ATG) polyclonal antibody, azathioprine, BAS1 L1X1MAB® (anti-I L-2Ra receptor antibody), cyclosporin (cyclosporin A), DACLIZUMAB® (anti-I L-2Ra receptor antibody), everolimus, mycophenolic acid, RITUX1MAB® (anti-CD20 antibody), sirolimus, tacrolimus, Tacrolimus and or Mycophenolate mofetil.

Antibiotics may be administered to the subject prior to, concurrently with and/or following treatment. Examples of antibiotics include Oflox, Gentamicin, Chloramphenicol, Tobrex, Vigamox or any other topical antibiotic preparation authorized for ocular use.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Derivation of RPE Cells without Generation of Spheroid Bodies (Laminin)

Materials and Methods

Figure 1:
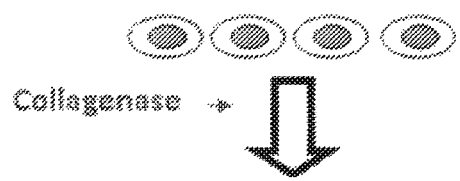
FIG. 1 is a pictorial representation of the process for derivation of retinal pigment epithelium (RPE) cells according to embodiments of the present invention.
Figure 1:
Figure 1:
Figure 1:

RPE cells were manufactured from HAD-C 102 hESCs that were manually expanded on human umbilical cord feeders (hUCFs; cord 008) in center well plates that were then passaged using collagenase onto feeder free Laminin 521 (5 µg/ml for 2 hr at 37° C.; Biolamina, Lam-521) coated flasks and grown with Nutristem™ containing HSA medium that contains bFGF and TGFβ (Biological Industries, 05-100-1A). On day 6 of hESC growth on Laminin 521, differentiation was initiated by replacing medium to Nutristem Minus (without bFGF and TGFβ; Biological Industries, 06-5102-01-1A) that contained 10 mM nicotinamide (Sigma, N-5535) for one week (medium was replaced at day 9) followed by 2 weeks with Nutristem Minus that contained 10 mM nicotinamide and 140 ng/ml Activin A (Peprotech, G-120-14E) and ~1 week with Nutristem Minus that contained 10 mM nicotinamide until patches of pigmented cells were observed. Then cells were harvested using TrypLE select (Invitrogen, 12563-011), filtered through a 40 µm strainer and centrifuged. Viable cells were counted and seeded in 3 recombinant human gelatin (rhGelatin, Fibrogen RhG100-001) coated wells (of a 6-well plate) in the presence of DMEM (HyClone, SH30081) containing 20% human serum (Akron, AK9905) for up to 3 days and for up to 11 days in the presence of Nutristem Minus. Viable cells were then harvested at the end of passage 0 (P0, at day 10) and seeded in T75 flask w\o rhGelatin with 20% human serum medium in the presence of DMEM containing 20% human serum for up to 3 days and for up to day 11 in the presence of Nutristem Minus. This step was repeated once again and cells at the end of passage 2 were harvested and cryopreserved. Schematic presentation of the process can be found in FIG. 1.

Results

Patches of pigmented cells were generated at the end of the differentiation process (FIG. 2A, yellow arrows). Following harvesting of all cells with TrypLE Select, filtration trough a 40 μm strainer and one expansion step, cells with polygonal morphology covered the entire cell culture plate (FIG. 2B, cells at the end of P0).

Figure 3A:
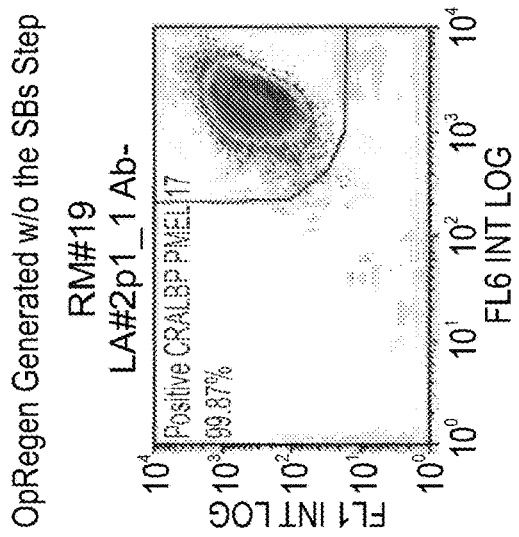
FIGS. 3A-C are graphs illustrating the purity of hESC derived pigmented/polygonal cells generated without spheroid bodies as measured by FACS analysis.
Figure 3B:
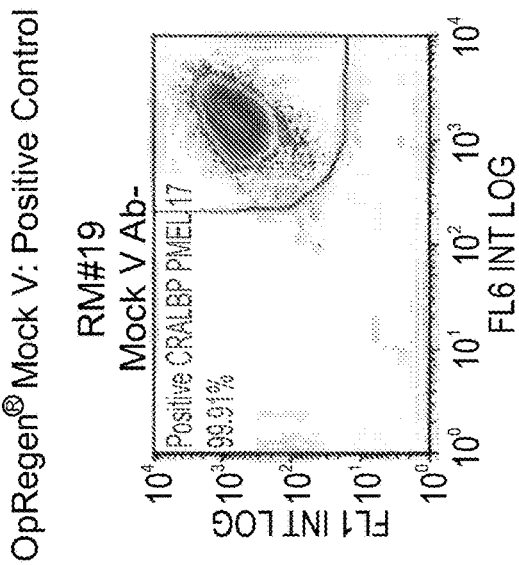
Figure 3C:
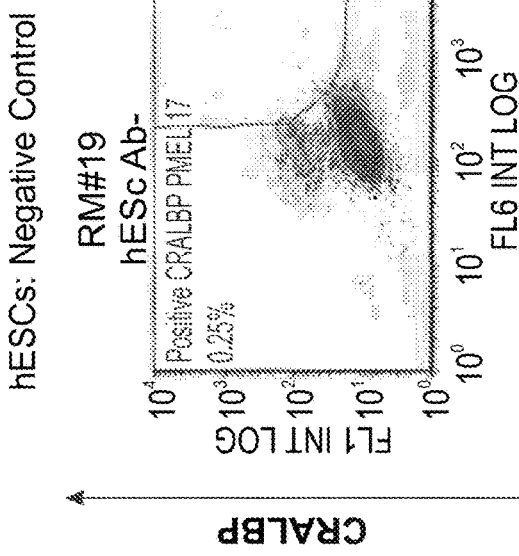
Figure 4C:
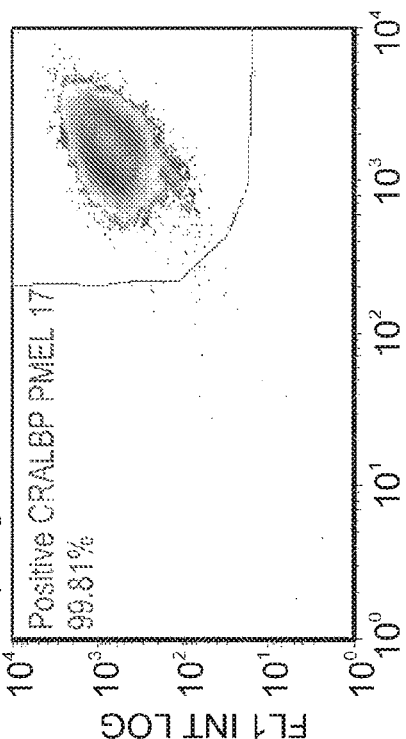
Figure 4C:
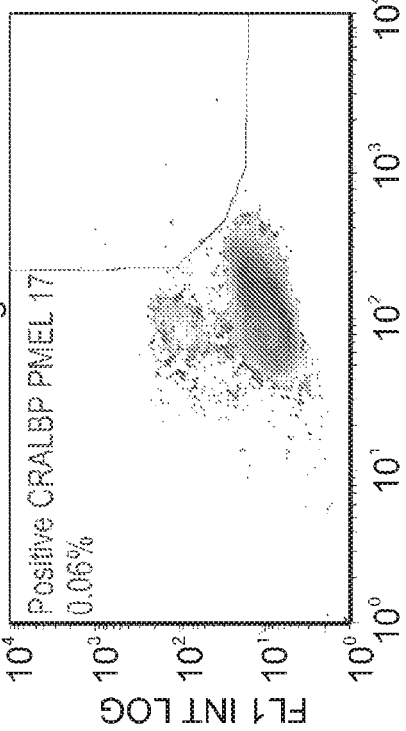
Figure 4D:
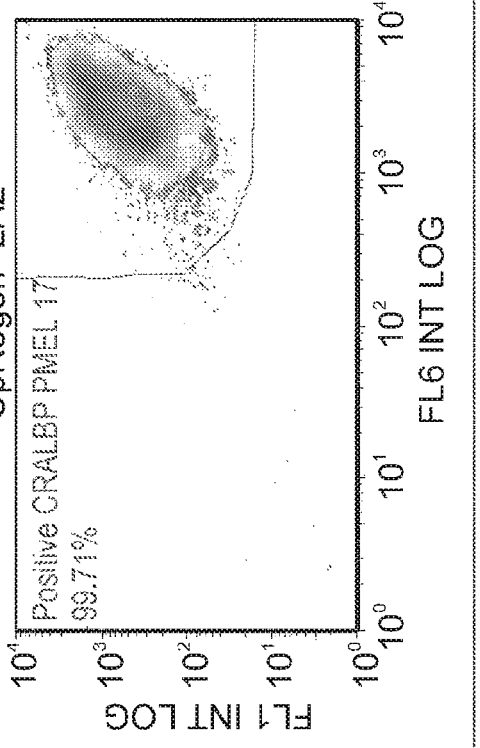

At the end of P1, cells were tested for identity/purity using the CRALBP/PMEL17 double staining FACS assay. As shown in FIGS. 3A-C, above 99% of the cells were double positive for CRALBP and PMEL17.

At the end of P2, cells were tested for identity/purity using the CRALBP/PMEL17 double staining FACS assay. As shown in FIGS. 4A-D, above 99% of the cells were double positive for CRALBP and PMEL17.

Example 2

Derivation of RPE Cells without Generation of Spheroid Bodies (Vitronectin)

Materials and Methods

RPE cells were manufactured from HAD-C 102 hESCs that were manually expanded on human umbilical cord feeders (hUCFs; cord 008) in center well plates that were then passaged using collagenase onto feeder-free, vitronectin (5-10 μg/200 ml PBS per well of 6 well plate) coated flasks and grown with Nutristem™ containing HSA medium that contains bFGF and TGFβ (Biological Industries, 05-100-1A). In some experiments, the undifferentiated hESCs were passaged with collagenase and replated on vitronectin for further expansion in the same medium. On day 6 or 7 of hESC growth on vitronectin, differentiation was initiated by replacing medium to Nutristem Minus (without bFGF and TGFβ; Biological Industries, 06-5102-01-1A) that contained 10 mM nicotinamide (Sigma, N-5535) for two weeks (medium was replaced at day 9) followed by 2 weeks with Nutristem Minus that contained 10 mM nicotinamide and 140 ng/ml Activin A (Peprotech, G-120-14E) and ~1 week with Nutristem Minus that contained 10 mM nicotinamide until patches of pigmented cells were observed. The whole culture was harvested using Triple Select. Viable cells were counted and seeded in 3 recombinant human gelatin (rhGelatin, Fibrogen RhG100-001) coated wells (of a 6-well plate) in the presence of DMEM (HyClone, SH30081) containing 20% human serum (Akron, AK9905) for up to 3 days and for up to 11 days in the presence of Nutristem Minus. Viable cells were then harvested at the end of passage 0 (P0, at day 10) and seeded in T75 flask w\o rhGelatin with 20% human serum medium in the presence of DMEM containing 20% human serum for up to 3 days and for up to day 11 in the presence of Nutristem Minus. This step was repeated once again and cells at the end of passage 2 were harvested and cryopreserved. The experiment was repeated 4 times, twice under low oxygen concentrations and twice under normal oxygen concentrations.

Results

Figure 5A:
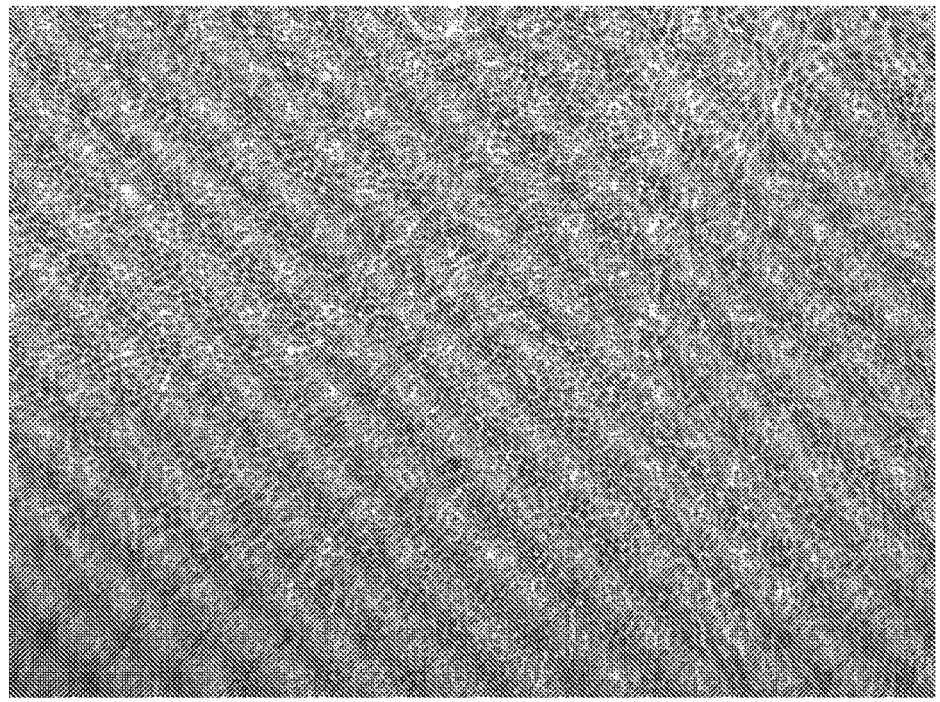
FIGS. 5A-C are representative phase contrast images of RPE cells derived on vitronectin.
Figure 5B:
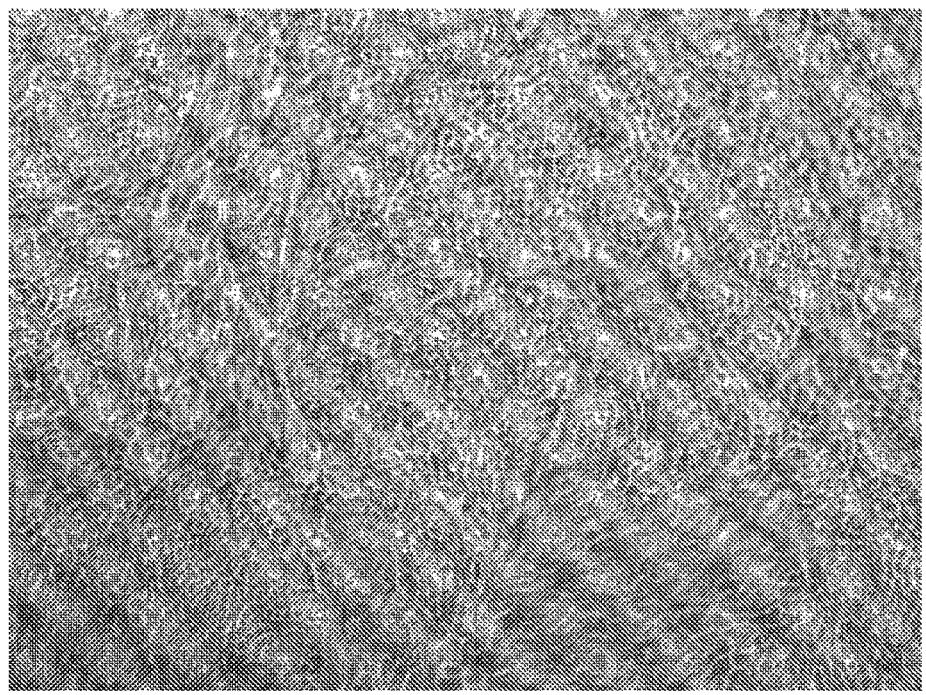
Figure 5C:
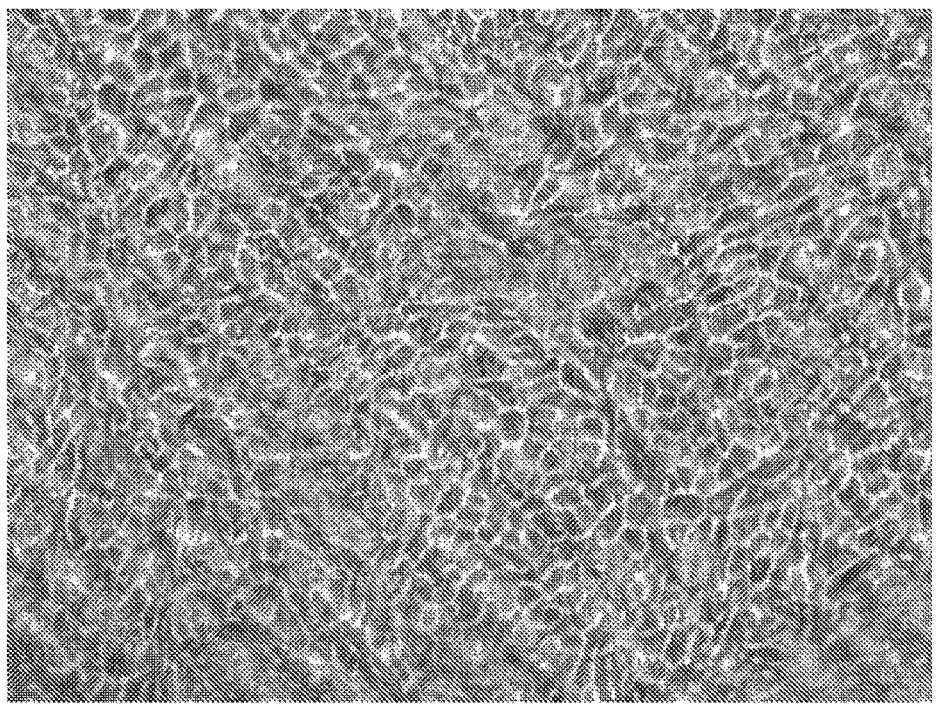
Figure 6A:
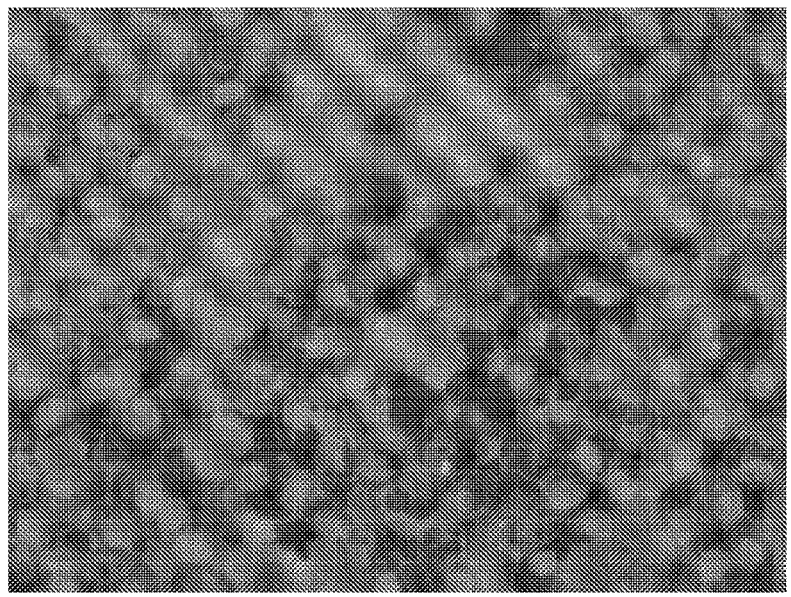
FIGS. 6A-E are immunofluorescence images of RPE cells derived on vitronectin decorated by antibodies identifying RPE markers. The majority of cells in the images express the markers of RPE cells (X40).
Figure 6B:
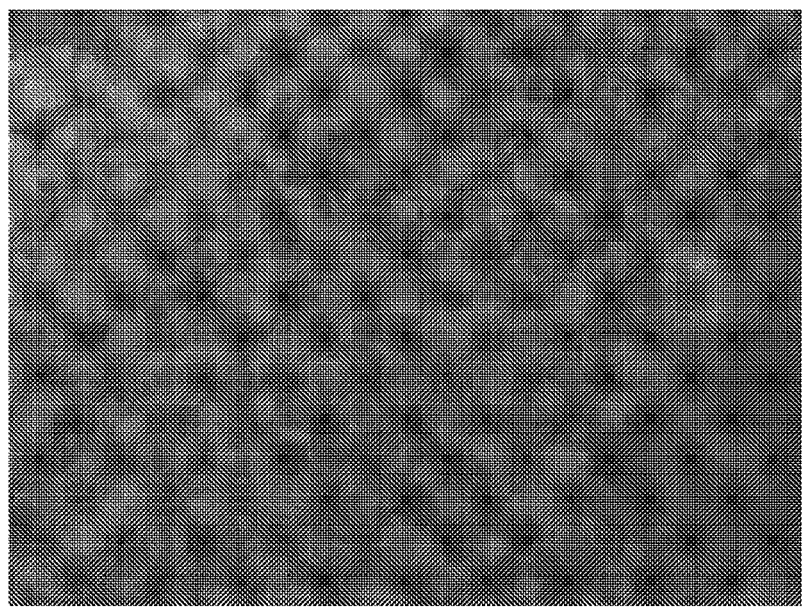
Figure 6C:
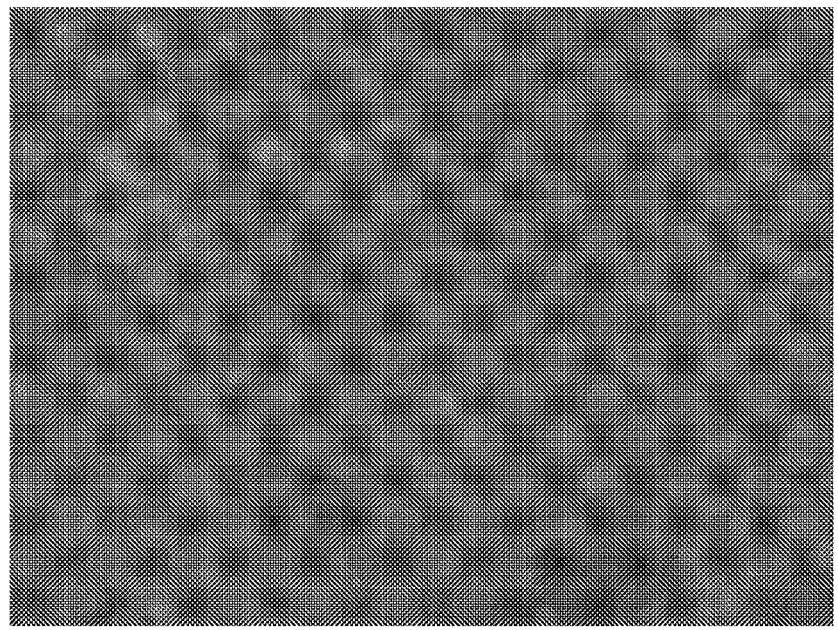
Figure 6D:
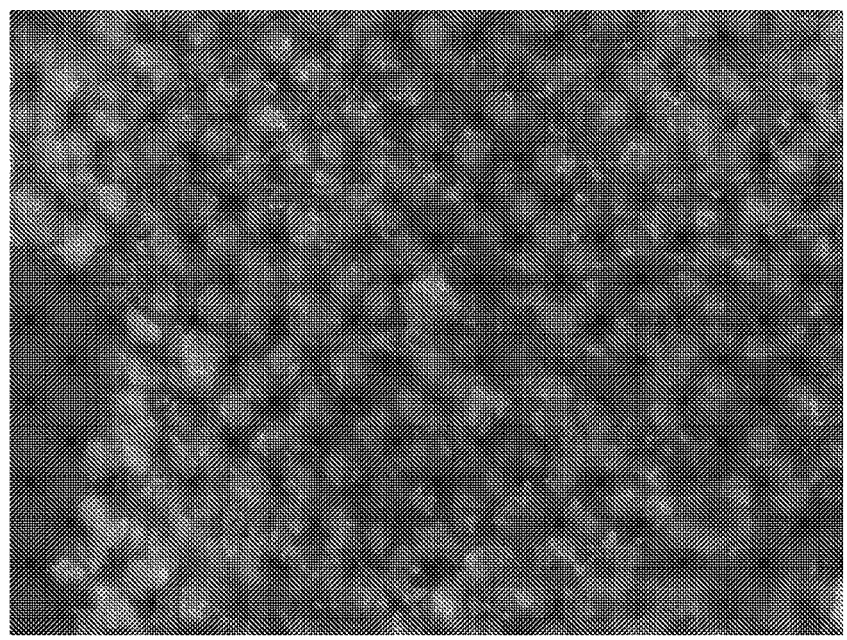
Figure 6E:
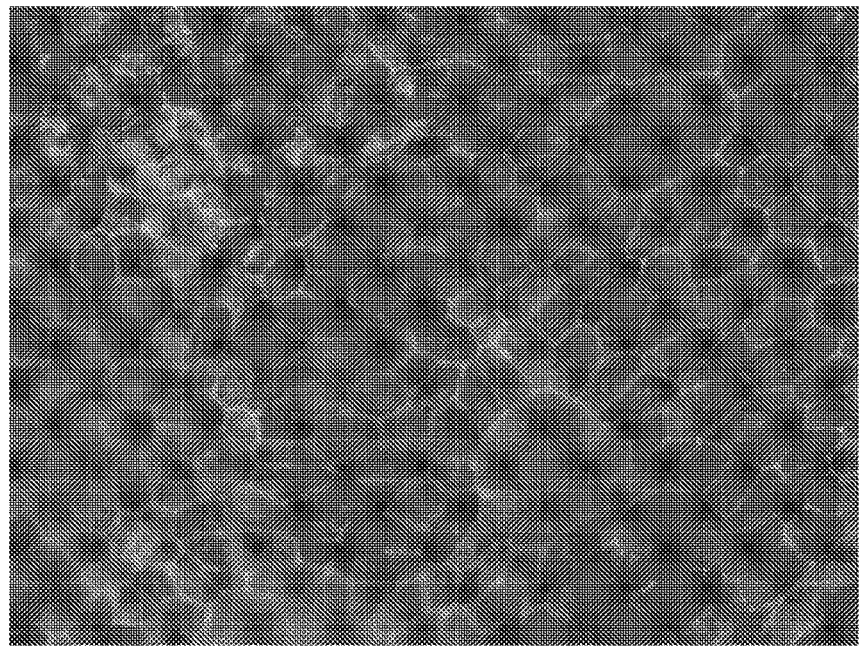

Patches of pigmented cells were generated at the end of the differentiation process. The whole culture was harvested by enzymatic digestion and replated for further culture and expansion under conditions that promote RPE cell growth. Cells with polygonal morphology covered the entire cell culture plates. The majority of cells harbor dark pigmentation (FIGS. 5A-C). Immunostaining showed that the majority of cells expressed markers of RPE cells including bestrophin, CRALBP, MITF, PEDF and ZO-1 (FIGS. 6A-E).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating retinal pigment epithelial (RPE) cells, the method comprising:
    (a) differentiating a population of undifferentiated human pluripotent stem cells on an adherent surface comprising at least one molecule selected from the group consisting of laminin, fibronectin, vitronectin, collagen I and collagen IV and under feeder cell free conditions in a medium comprising between 1 mM and 100 mM nicotinamide as a differentiating agent to obtain differentiating cells, wherein between about 50%-100% of the cells of said population of undifferentiated human pluripotent stem cells are Oct4+TRA-1-60+; and
    (b) further differentiating said differentiating cells on said adherent surface for 1 day to 2 weeks in a medium which comprises between 1 mM and 100 mM nicotinamide, and between 20 and 200 ng/ml Activin A;
    (c) further differentiating the cells obtained from step (b) in a medium comprising nicotinamide and devoid of Activin A to obtain a culture of differentiated cells comprising pigmented and non-pigmented cells;
    (d) enzymatically harvesting the culture of differentiated cells from said adherent surface to obtain a population of isolated differentiated cells; and
    (e) expanding the population of isolated differentiated cells to obtain an expanded population of differentiated cells, wherein at least 70% of the expanded population of differentiated cells are CRALBP+PMEL17+, thereby generating RPE cells,
    wherein at least one of step (a) or step (b) occurs in 1% to 10% oxygen.

2. The method of claim 1, further comprising expanding said population of undifferentiated human pluripotent stem cells on said adherent surface in the absence of said differentiating agent prior to step (a).

3. The method of claim 1, wherein said adherent surface is laminin 521.

4. The method of claim 1, wherein expanding the population of isolated differentiated cells is carried out on an additional adherent surface and wherein said additional adherent surface comprises gelatin, poly-d-lysine, laminin, collagen I, collagen IV, or a combination thereof.

5. The method of claim 1, wherein said human pluripotent stem cells comprise human embryonic stem cells.

6. The method of claim 1, wherein said medium of step (a) is devoid of activin A.

7. The method of claim 1, wherein the medium of step (b) further comprises one or more additional members of the TGFβ superfamily.

8. The method of claim 7, wherein said one or more additional members of the TGFβ superfamily is TGFβ1 or TGFβ3.

9. The method of claim 1, wherein the isolated RPE cells of step (d) are purified using a filter.

10. The method of claim 1, wherein step (a) occurs for 1 day to 2 weeks.

11. The method of claim 1, wherein step (c) occurs for 1 day to 21 days.

12. The method of claim 1, wherein step (e) occurs in the absence of nicotinamide.

13. The method of claim 1, wherein step (e) comprises a first expansion period (P0), a second expansion period (P1) and a third expansion period (P2).

14. The method of claim 13, wherein the first expansion period occurs for 10-14 or 7-21 days.

15. The method of claim 13, wherein the second expansion period occurs for 10-14 or 7-21 days.

16. The method of claim 13, wherein the third expansion period occurs for 10-14 or 7-21 days.

17. The method of claim 1, wherein pigmented cells are not isolated from the cells obtained from step (b) prior to step (c).

18. The method of claim 1, wherein step (c) comprises:
   (i) differentiating the cells in 1% to 10% oxygen for up to 7 days, followed by
   (ii) differentiating the cells in about 20% oxygen.

19. A method of generating retinal pigment epithelial (RPE) cells, the method comprising:
   (a) differentiating a population of undifferentiated human pluripotent stem cells on an adherent surface comprising at least one molecule selected from the group consisting of laminin, fibronectin, vitronectin, collagen I and collagen IV, and under feeder cell free conditions, without using cells comprising spheroid or embryoid bodies, in a medium comprising between 1 mM and 100 mM nicotinamide as a differentiating agent to obtain differentiating cells, wherein at least between about 50%-100% of the cells of the population of undifferentiated human pluripotent stem cells are Oct4+ TRA-1-60+;
   (b) further differentiating said differentiating cells on said adherent surface for 1 day to 2 weeks, without using cells comprising spheroid or embryoid bodies, in a medium comprising between 1 mM and 100 mM nicotinamide and between 20 ng/ml and 200 ng/ml Activin A;
   (c) further differentiating the cells from step (b) in a medium comprising nicotinamide and devoid of Activin A to obtain a culture of differentiated cells comprising pigmented and non-pigmented cells;
   (d) enzymatically harvesting the culture of differentiated cells from said adherent surface to obtain a population of isolated differentiated cells; and
   (e) expanding the population of isolated differentiated cells to obtain an expanded population of differentiated cells, wherein at least 70% of the expanded population of differentiated cells are CRALBP+PMEL17+, thereby generating RPE cells,
   wherein at least one of step (a) or step (b) occurs in 1% to 10% oxygen.

20. The method of claim 19, wherein cells of the expanded population of differentiated cells comprise a polygonal morphology.

21. The method of claim 19, wherein the isolated RPE cells of step (d) are purified using a filter.

22. A method of generating retinal pigment epithelial (RPE) cells, the method comprising:
   (a) differentiating a population of undifferentiated human pluripotent stem cells on an adherent surface comprising at least one molecule selected from the group consisting of laminin, fibronectin, vitronectin, collagen I and collagen IV and under feeder cell free conditions in a medium comprising between 1 mM and 100 mM nicotinamide as a differentiating agent to obtain differentiating cells, wherein between about 50%-100% of the cells of said population of undifferentiated human pluripotent stem cells are Oct4+TRA-1-60+; and
   (b) further differentiating said differentiating cells on said adherent surface for 1 day to 4 weeks in a medium which comprises between 1 mM and 100 mM nicotinamide, and between 20 and 200 ng/ml Activin A;
   (c) further differentiating the cells obtained from step (b) without isolating pigmented cells in a medium comprising nicotinamide and devoid of Activin A to obtain a culture of differentiated cells comprising pigmented and non-pigmented cells;
   (d) enzymatically harvesting the culture of differentiated cells from said adherent surface to obtain a population of isolated differentiated cells; and
   (e) expanding the population of isolated differentiated cells to obtain an expanded population of differentiated cells, wherein at least 70% of the expanded population of differentiated cells are CRALBP+PMEL17+, thereby generating RPE cells,
   wherein at least one of step (a) or step (b) occurs in 1% to 10% oxygen.

23. A method of generating retinal pigment epithelial (RPE) cells, the method comprising:
   (a) differentiating a population of undifferentiated human pluripotent stem cells on an adherent surface comprising at least one molecule selected from the group consisting of laminin, fibronectin, vitronectin, collagen I and collagen IV and under feeder cell free conditions in a medium comprising between 1 mM and 100 mM nicotinamide as a differentiating agent for between 1 day and 2 weeks to obtain differentiating cells, wherein between about 50%-100% of the cells of said population of undifferentiated human pluripotent stem cells are Oct4+TRA-1-60+; and
   (b) further differentiating said differentiating cells on said adherent surface for 1 day to 4 weeks in a medium which comprises between 1 mM and 100 mM nicotinamide, and between 20 and 200 ng/ml Activin A;
   (c) further differentiating the cells obtained from step (b) in a medium comprising nicotinamide and devoid of Activin A to obtain a culture of differentiated cells comprising pigmented and non-pigmented cells;

(d) enzymatically harvesting the culture of differentiated cells from said adherent surface to obtain a population of isolated differentiated cells; and (e) expanding the population of isolated differentiated cells to obtain an expanded population of differentiated cells, wherein at least 70% of the expanded population of differentiated cells are CRALBP+PMEL17+, thereby generating RPE cells, wherein at least one of step (a) or step (b) occurs in 1% to 10% oxygen.

24. A method of generating retinal pigment epithelial (RPE) cells, the method comprising:
(a) differentiating a population of undifferentiated human pluripotent stem cells on an adherent surface comprising at least one molecule selected from the group consisting of laminin, fibronectin, vitronectin, collagen I and collagen IV and under feeder cell free conditions in a medium comprising between 1 mM and 100 mM nicotinamide as a differentiating agent to obtain differentiating cells, wherein between about 50%-100% of the cells of said population of undifferentiated human pluripotent stem cells are Oct4+TRA-1-60+; and
(b) further differentiating said differentiating cells on said adherent surface for 1 day to 4 weeks in a medium which comprises between 1 mM and 100 mM nicotinamide, and between 20 and 200 ng/ml Activin A;
(c) further differentiating the cells obtained from step (b) in a medium comprising nicotinamide and devoid of Activin A for between 1 day and 21 days to obtain a culture of differentiated cells comprising pigmented and non-pigmented cells;
(d) enzymatically harvesting the culture of differentiated cells from said adherent surface to obtain a population of isolated differentiated cells; and
(e) expanding the population of isolated differentiated cells to obtain an expanded population of differentiated cells, wherein at least 70% of the expanded population of differentiated cells are CRALBP+PMEL17+, thereby generating RPE cells, wherein at least one of step (a) or step (b) occurs in 1% to 10% oxygen.

25. A method of generating retinal pigment epithelial (RPE) cells, the method comprising:
(a) differentiating a population of undifferentiated human pluripotent stem cells on an adherent surface comprising at least one molecule selected from the group consisting of laminin, fibronectin, vitronectin, collagen I and collagen IV and under feeder cell free conditions in a medium comprising between 1 mM and 100 mM nicotinamide as a differentiating agent for between 1 day and 2 weeks to obtain differentiating cells, wherein between about 50%-100% of the cells of said population of undifferentiated human pluripotent stem cells are Oct4+TRA-1-60+; and
(b) further differentiating said differentiating cells on said adherent surface for 1 day to 2 weeks in a medium which comprises between 1 mM and 100 mM nicotinamide, and between 20 and 200 ng/ml Activin A;

(c) further differentiating the cells obtained from step (b) without isolating pigmented cells in a medium comprising nicotinamide and devoid of Activin A for between 1 day and 21 days to obtain a culture of differentiated cells comprising pigmented and non-pigmented cells;
(d) enzymatically harvesting the culture of differentiated cells from said adherent surface to obtain a population of isolated differentiated cells; and
(e) expanding the population of isolated differentiated cells to obtain an expanded population of differentiated cells, wherein at least 70% of the expanded population of differentiated cells are CRALBP+PMEL17+, thereby generating RPE cells, wherein at least one of step (a) or step (b) occurs in 1% to 10% oxygen.

26. The method of claim 25, wherein step (a) occurs in 1% to 10% oxygen.

27. The method of claim 25, wherein step (b) occurs in 1% to 10% oxygen.

28. The method of claim 25, wherein step (c) comprises:
(i) differentiating the cells in 1% to 10% oxygen for up to 7 days, followed by
(ii) differentiating the cells in about 20% oxygen.

29. A method of generating retinal pigment epithelial (RPE) cells, the method comprising:
(a) differentiating a population of undifferentiated human pluripotent stem cells on an adherent surface comprising at least one molecule selected from the group consisting of laminin, fibronectin, vitronectin, collagen I and collagen IV and under feeder cell free conditions in a medium comprising between 1 mM and 100 mM nicotinamide as a differentiating agent to obtain differentiating cells, wherein between about 50%-100% of the cells of said population of undifferentiated human pluripotent stem cells are Oct4+TRA-1-60+; and
(b) further differentiating said differentiating cells on said adherent surface for 1 day to 4 weeks in a medium which comprises between 1 mM and 100 mM nicotinamide, and between 20 and 200 ng/ml Activin A;
(c) further differentiating the cells obtained from step (b) in a medium comprising nicotinamide and devoid of Activin A to obtain a culture of differentiated cells comprising pigmented and non-pigmented cells;
(d) enzymatically harvesting the culture of differentiated cells from said adherent surface to obtain a population of isolated differentiated cells; and
(e) expanding the population of isolated differentiated cells to obtain an expanded population of differentiated cells, wherein at least 70% of the expanded population of differentiated cells are CRALBP+PMEL17+ and wherein step (e) occurs in the absence of nicotinamide, thereby generating RPE cells, wherein at least one of step (a) or step (b) occurs in 1% to 10% oxygen.

\* \* \* \* \*